United States Patent [19]
Bogard, Jr. et al.

[11] Patent Number: 5,179,018
[45] Date of Patent: * Jan. 12, 1993

[54] MAMALIAN MONOCLONAL ANTIBODIES AGAINST ENDOTOXIN OF GRAM-NEGATIVE BACTERIA

[75] Inventors: Warren C. Bogard, Jr., West Chester; Patrick C. Kung, Villanova, both of Pa.

[73] Assignee: Centocor, Inc., Malvern, Pa.

[*] Notice: The portion of the term of this patent subsequent to Oct. 15, 2008 has been disclaimed.

[21] Appl. No.: 542,111

[22] Filed: Oct. 14, 1983

[51] Int. Cl.$^5$ .................... C12N 5/22; C12N 15/02; C07K 15/28
[52] U.S. Cl. ................... 530/388.15; 435/172.2; 435/240.2; 435/240.27; 530/388.4; 530/865
[58] Field of Search ............... 424/1.1, 9.85, 177.87; 436/510, 518, 536, 542, 548, 804, 811, 815; 435/4, 7, 68, 70, 172, 240, 948, 240.27, 240.2, 172.2; 260/112 R; 530/387; 241/177

[56] References Cited

U.S. PATENT DOCUMENTS

| | | | |
|---|---|---|---|
| 4,443,549 | 4/1984 | Sadowski | 436/548 |
| 4,451,570 | 5/1984 | Royston | 435/240 |
| 4,455,296 | 6/1984 | Hansen | 424/88 |
| 4,464,465 | 8/1984 | Lostrum | 435/68 |

FOREIGN PATENT DOCUMENTS

| | | |
|---|---|---|
| 0174204 | 3/1986 | European Pat. Off. |
| 86306420 | 8/1986 | European Pat. Off. |
| WO/84/04458 | 11/1984 | PCT Int'l Appl. |
| WO/85/01659 | 4/1985 | PCT Int'l Appl. |

OTHER PUBLICATIONS

Kaplan, H. S. et al. *Monoclonal Antibodies in Clinical Medicine*, McMichael, A. J. et al., eds., Academic Press (1982) N.Y.; pp. 17–35.
Nowinski, R. C. et al., *Science*, 219:637–644 (Feb. 1983).
Wolf, G. L. et al., *Magnetic Resonance Annual* (1985), Kressel, H. Y. ed., Raven Press, N.Y. pp. 231–266.
Abrams, P. G. et al. *J. of Immunol.*, vol. 131(3), pp. 1201–1204 (Sep. 1983).
Marks, M. I. et al., *J. Clin. Invest.*, vol. 69(4), pp. 742–749 (Apr. 1982).
Howard, J. C. et al., *Immunol. Rev.*, vol. 47, pp. 160–174 (1979).
Hughes-Jones, N. C. et al., *Eur. J. Immunol.*, vol. 13, pp. 635–641 (1983).
Pollack, M. et al., Abstracts 1983 Interscience Conf. Antimicrob. Agents Chemother., Abs. 614, p. 195 (Aug. 1983).
Hiernaux, J. et al., *Proc. Natl. Acad. Sci., U.S.A.*, vol. 79, pp. 1616–1620 (Mar. 1982).
Hiernaux, J. R. et al., *Eur. J. Immunol.*, vol. 12(10), pp. 797–803 (1982).
Morse, S. A. et al., *J. Infect. Diseases*, vol. 145(2) pp. 206–216 (Feb. 1982).
Young, L. S. et al., *Clinical Research*, p. 522A, vol. 30 (2), (1982).
Braude, A. I. et al., *J. Infect. Diseases*, vol. 136, pp. S167–S173 (1977).
McCabe, W. R. et al., *J. Infect. Diseases*, vol. 136, pp. S164–S166 (1977).
Ziegler, E. J. et al., *New England J. Medicine*, vol. 307, (20), pp. 1225–1230 (Nov. 1982).
Kozbor, D. et al., *Immunology Today*, vol. 4(3), pp. 72–79 (1983), Applicants' Attachment A.
Levy, R. et al., *Ann. Rev. Med.*, vol. 34, pp. 107–116 (1983), Applicants' Attachment E.
Miller, R. A. et al., *The Lancet*, Aug. 1, 1981, pp. 226–230, Applicants' Attachment F.
Sears, H. F. et al., *The Lancet*, Apr. 3, 1982, pp. 762–765, Applicants' Attachment G.
Dillman, R. O. et al., *Blood*, vol. 59(5), pp. 1036–1045 (1982), Applicants' Attachment H.
Hiernaux, J. et al., *Proc. Natl. Acad. Sci., U.S.A.*, vol. 79, pp. 1616–1620 Mar. 1982.
Darveau, R. P. et al., *J. Bacteriology*, vol. 155(2), pp. 831–838 (1983).
Sugaswara, R. J. et al., *Infec. Immun.*, vol. 42(3), pp. 863–868 (1983), Biosis Abstract 77059416.
Hancock, R. E. W. et al., *Infec. Immun.*, vol. 37(1), pp. 166–171 (1982).
Hiernaux, J. R. et al., *Eur. J. Immunol.*, vol. 12(10), pp. 797–803 (1982).
Abe et al., *Jpn. J. Exp. Med.* (1975) 45:355–359.
Feingold et al., *Arch. Int. Med.* (1965) 116:326–328.
Hancock et al., *Infect. Immun.* (1982) 37:166–171.
Hiernaux et al., *Eur. J. Immunology* (1982) 12:797–803.
Kohler et al., *Nature* (1975) 256:495–497.
Mackie et al., *J. Immunol.* (1982) 129:829–832.
Young, L. S., *Principles and Practice of Infectious Disease*, (1985) John Wiley and Sons, N.Y., 452–475.
Young et al., *Clinical Research* (1982) 30:522A.
Zeigler et al., *N. Eng. J. Med.* (1982) 307:1225–1230.
Olsson et al., *Proc. Natl. Acad. Sci.* (1980) 77:5429–5431.

*Primary Examiner*—John Doll
*Assistant Examiner*—Jeff Kushan
*Attorney, Agent, or Firm*—Hamilton, Brook, Smith & Reynolds

[57] ABSTRACT

Mammalian monoclonal anti-lipopolysaccharide (LPS) antibodies which react with gram-negative bacteria across different genera are disclosed. The anti-LPS antibodies are useful for the treatment or prevention of gram-negative bacteremia and for the detection of gram-negative microorganisms.

3 Claims, 4 Drawing Sheets

MAMALIAN MONOCLONAL ANTIBODIES AGAINST ENDOTOXIN OF GRAM-NEGATIVE BACTERIA

FIELD OF THE INVENTION

This invention is in the fields of immunology and microbiology and pertains to mammalian monoclonal antibodies which react with antigenic determinants of lipopolysaccharide (LPS) of gram-negative bacteria which are shared by gram-negative bacteria of different genera.

BACKGROUND OF THE INVENTION

In the last twenty years, gram-negative bacteria have become the leading agents of fatal bacterial infections in hospital patients. Each year nosocomial (hospital-acquired) bacteremia develops in approximately 194,000 patients in U.S. hospitals; of these about 75,000 die. Maki, D. G., (1981) in *Nosocomial Infections* (Dixon, R. E., Ed.), pp. 183–196, Yorke Medical Books, U.S.A. In this recent epidemiological review of nosocomial infections, it was reported that six major gram-negative bacilli accounted for most etiological agents; they are: *Escherichia coli, Pseudomonas aeruginosa, Proteus, Klebsiella, Enterobacter,* and *Serratia.*

At present, antibiotics are the chief weapons in combating the nosocomial infection. However, antibiotic therapy does not seem to lower the death rate very significantly for gram-negative bacteremia. Braude et al., (1977) *J. Infect. Dis.* 136, S167–173. The shortcomings of antibiotics might be attributed to the impermeability of the outer membrane of the gram-negative bacteria to the drugs and to their inability to counteract the lethal shocks caused by bacterial endotoxin.

In the last decade, several groups have attempted to develop passive immunization as an alternative or supplement to antibiotics for the control of nosocomial infections. It was expected that antiserum against endotoxin could prevent and reverse the effects of the toxin and could facilitate the removal of gram-negative bacteria from the circulation by the reticulo-endothelial system.

Because the clinical picture of shock from gram-negative bacterial septicemia is identical to that induced experimentally with endotoxin, shock resulting from gram-negative bacteremia is often referred to as "endotoxin shock." This is believed to be because the endotoxin is present on the surface of the outer membrane of gram-negative bacteria, and thus is in a position to react with body fluids and to cause the same disturbances as those seen after injection of endotoxin.

The endotoxins of gram-negative bacteria are lipopolysaccharides (LPS). There are at least three major antigenic regions in endotoxins. Luderitz et al., (1982) *Curr. Top. Membr. Transp.* 17, 79–151. Theoretically each is a target for a protective antibody or anti-endotoxin. The three antigenic regions of LPS are lipid A, core polysaccharide and O-specific polysaccharide (also referred to as O-specific chain or simply O-antigen). A schematic representation of LPS is shown in FIG. 1A. The O-specific polysaccharide vary markedly with each species and serologic type of bacteria. The lipid A and core polysaccharide of most gram-negative bacteria, however, share similar, if not identical, structures. This is especially true of the region on either side of the core-lipid A junction. This area of LPS virtually always contains phosphate, 2-keto-3-deoxy-D-manno-octonate (KDO) and D-glucosamine, and usually contains L-glycerol-D-manno-heptose (see FIG. 1B).

In rough strains of bacteria, the O-specific polysaccharide is lost through a mutation that deprives the bacteria of either the enzymes required to synthesize the O-antigen or the enzyme required to attach them to the core. Ziegler and co-workers exploited this genetic change to develop conventional (polyclonal) antisera against the uncovered core region on the assumption that antibody to the core of LPS would react uniformly with the endotoxins of all gram-negative bacteria because their core antigens are similar. Ziegler et al., (1973) *J. Immunol.* 111, 433–438. In order to produce antibody to core glycolipid, they prepared a vaccine from a rough mutant of *E. coli* 0111:B$_4$, known as J5. This *E. coli* mutant has a similar LPS chemotype (core carbohydrate chain length) to that of *S. minnesota* Rc LPS (FIG. 1C). The rabbit antiserum obtained after immunization was designated J5 antiserum. During the past eight years this group has shown that J5 antiserum can prevent the toxic actions of endotoxins from various gram-negative bacteria and protect against lethal bacteremia in immunosuppressed animals.

Using a similar approach, McCabe and colleagues showed that rabbit antisera to Re rough mutant of *Salmonella minnesota* (FIG. 1C) protected granulocytopenic rabbits against lethal bacteremia, and protected mice against lethal challenge with heterologous endotoxins. McCabe et al., (1977) *J. Infect. Dis.* 136, S161–166. In a separate study, a polyvalent human gamma-globulin against *Pseudomonas aeruginosa* protected mice against the lethal infections. This antisera elicited almost no cross protection. Fisher, M. W., (1977) *J. Infect. Dis.* 136, S181–185.

Very recently anti-core glycolipid of the LPS was prepared by vaccinating human subjects. Zeigler et al., (1982) *N. Eng. J. Med.* 307, 1225–1230. When the antisera was administered to gravely ill bacteremic patients, the death rate from bacteremia was virtually halved as compared to controls. Among patients in profound gram-negative shock, the rate of recovery rose from 24% in controls to 54% in those treated with the antiserum. Preliminary data indicated that the human antiserum used for prophylaxis could reduce the fever, morbidity and bacteremia in neutropenic patients with gram-negative infections.

However, the protection mechanism of the anti-LPS serum demonstrated in the aforementioned reports remains poorly understood. In some cases the opposite effect was observed. Davis et al., (1969) *J. Immunol.* 102, 563–572, found, for example, that rat antiserum to LPS induced lethal hypersensitivity to endotoxin in mice, while in the same report they found that rabbit antisera to LPS lowered the death rate from endotoxin. In summary, the observed protective effect could be variable, depending on the composition and titer of the conventional antisera used, the exact strain of bacteria tested, the route of antigen or antibody administration, and the protocols used in serotherapy.

To circumvent the variable efficacy of conventional antisera in the serotherapy, Young et al., (1982) *Clin. Research* 30, 522a, prepared monoclonal antibodies using *S. minnesota* R595 LPS as the immunogen. They were found to be only modestly protective against a single species of gram-negative bacteria in their animal model of bacteremia.

Although lipid A moiety of LPS is known to be necessary for the endotoxin activity, the exact antigenic determinant(s) on the lipid A responsible for the toxicity has remained obscure. Luderitz et al. supra.

SUMMARY OF THE INVENTION

This invention relates to mammalian monoclonal anti-LPS antibodies that react with regions of lipopolysaccharide which are common to the lipopolysaccharide molecules of gram-negative bacteria of different genera, and to diagnostic and therapeutic uses of the anti-LPS antibodies. The monoclonal anti-LPS antibodies of this invention react with gram-negative bacteria across different genera. The widespread cross reactivity of the antibodies may be attributed to the fact that the antibodies react with regions of the lipid A and/or the core of gram negative bacterial endotoxin which are shared by virtually all types of gram-negative bacteria. Importantly, the anti-LPS antibodies of this invention protect mice against the lethal effect from gram-negative bacterial infection and further, the anti-LPS antibodies neutralize the lethal effect of the endotoxin of gram-negative bacteria in vivo. This invention also pertains to immortal antibody-producing cells such as mammalian hybridoma cell lines which generate the monoclonal anti-LPS antibodies.

The mammalian monoclonal anti-LPS antibodies of this invention are useful in a number of diagnostic and therapeutic applications, including methods for the detection of gram-negative bacteria or endotoxin of gram-negative bacteria, therapy of gram-negative bacterial infection and endotoxin shock in mammals and prophylaxis against bacterial infection in mammals.

The hybridoma cell line HM22B arising from the fusion described above (i.e., fusion between human mononuclear cells and the human lymphoblastoid) was deposited under Budapest Treaty Patent Procedures at the American Type Culture Collection (ATCC) in Rockville, Md. This hybridoma cell line deposit has been assigned ATCC Designation Number HB 10947.

DETAILED DESCRIPTION OF THE INVENTION

The mammalian monoclonal anti-LPS antibodies of this invention react with gram-negative bacteria across genera. The antibodies specifically react with certain antigenic determinants on the LPS molecule, and these antigenic determinants are shared by most gram-negative bacteria. Unlike serotype-specific antibodies, the monoclonal antibodies of this invention bind to regions of the LPS molecule which are integral structural, and perhaps essential functional, components of the outer membrane of gram-negative microorganisms. Because of this, there is very little variation in these regions among different kinds of gram-negative bacteria; they are common to gram-negative bacteria of different genera, species and serotypes. Moreover mutations which might result in the elimination or significant alteration of these regions and consequently, the elimination of antibody reactivity, are unlikely to occur.

For example, some of the anti-LPS antibodies of this invention recognize and bind to the lipid A region of LPS. Lipid A is known to be an integral component of the outer membrane of all gram-negative bacteria; indeed, no mutant lacking lipid A is known to exist. In contrast to the O-antigen segment of LPS, which is highly variable, lipid A does not vary significantly among gram-negative bacteria of different serotype, species or genus. Consequently the anti-lipid A antibodies react with gram-negative bacteria across serotypes, species and genera.

Other anti-LPS antibodies of this invention react specifically with antigenic determinants on the core region of LPS or with antigenic determinants that overlap the core region and lipid A. Comparable to lipid A, the core region of LPS is also highly conserved among gram-negative bacteria and thus antibodies directed against this region of the LPS molecule also exhibit wide cross-reactivity with gram-negative bacteria.

The reactivity of the monoclonal antibodies with gram-negative bacteria is demonstrated by bacterial cell binding assays. The anti-LPS antibodies bind to a wide variety of gram-negative bacteria including *Escherichia coli, Salmonella minnesota, Klebsiella pneumonia, Pseudomonas aeruginosa* and *Serratia marcescens*, all of which represent distinct genera of bacteria. Moreover, these organisms are all pathogenic; in fact, epidemiological studies indicate that these five species account for at least two-thirds of all nosocomial gram-negative bacteremia. The antibodies show no reactivity with gram-positive microorganisms.

As with whole cell bacteria, the antibodies exhibit extensive cross-reactivity with LPS molecules. The anti-LPS antibodies react with purified LPS molecules of gram-negative bacteria, including all or most of the following: *E. coli* J5, *E. coli* 0111:B4, *E. coli* O55:B5, *S. minnesota, S. minnesota* R595. *K. pneumonia, P. aeruginosa* and *S. marcescens*. This indicates that the cross-reactivity of the anti-LPS antibodies to the whole cell bacteria is due to reactivity with the LPS molecule on the cell surface. Further, it appears that for those antibodies which react with determinants on the lipid A portion of LPS, these determinants are available on the surface of the bacteria for antibody binding.

In addition, the anti-LPS antibodies cross react with serotypically distinct strains of a particular species of gram-negative bacterium. For example, the antibodies bind to LPS molecules obtained from crude membrane preparations of all seventeen classically distinct serological strains of Pseudomonas aeruginosa. In contrast, a monoclonal antibody specific for O-antigen from P. aeruginosa International Antigen Typing Scheme (IATS) serotype 5 strain cross reacted only weakly with a serotype 17 strain and failed to react at all with LPS from strains representing the other 15 IATS serotypes. Hancock et al., (1982) Infect. Immun. 37, 166-171.

Further, certain of the anti-LPS antibodies bind to the LPS obtained from serologically unclassified strains of P. aeruginosa isolated from patients with cystic fibrosis. Thus, these monoclonal anti-LPS antibodies recognize LPS not only from all serologically distinct strains of P. aeruginosa but also from serologically unclassified natural isolates indicating that the anti-LPS antibodies recognize an antigenic determinant on the lipopolysaccharide molecule which is conserved in gram-negative bacteria and which is likely to be present in new unclassified strains of P. aeruginosa.

The monoclonal antibodies of this invention protect mice infected by gram-negative bacteria from the lethal effects of the microorganisms. The protective capabilities of the anti-LPS antibodies are manifest in two different model systems of bacteremia in mice, a direct sepsis model and a burn sepsis model. In the direct sepsis model, mice are injected with a mixture of antibodies and subsequently are infected intravenously with several serotypically distinct gram-negative bacteria. In the burn model, mice are burned with an alcohol flame and the damaged skin is inoculated with an extremely virulent strain of P. aeruginosa. The monoclonal anti-LPS antibodies are administered either in a single injection 24 hours before the burn or in two injections, one 24 hours before the burn and the other 20 hours after.

In both model systems, the monoclonal antibodies either prevent or delay death in mice. This is demonstrated for gram-negative bacteria of several different genera. In the direct sepsis model, most mice treated with antibodies were alive seven days after the inoculation with bacteria, while all mice which did not receive the antibodies perished within a few days. In all burned mice which received antibodies according to either regimen, survival was significantly prolonged. Notably, burned mice which received the anti-LPS antibodies were not moribund until the latter stages of their prolonged survival whereas those that did not receive the antibodies became moribund quickly. The eventual death of the mice may be attributed to the exhaustion of protective antibody. Repeated administration of the antibodies to these mice may prolong survival indefinitely.

It is suspected that the protective action of the anti-LPS antibodies is a result of the binding of the antibody to the bacterial cell. This binding may foster opsonization or activate complement. The opsonizing of bacterial cells with antibody promotes ingestion of the cells by granulocytes and macrophages. Activation of complement results in cell lysis.

The monoclonal anti-LPS antibodies can neutralize the lethal toxic effects of LPS in vivo. For instance, various mixtures of the monoclonal antibodies prolonged survival in mice which were injected with free lipid A or LPS derived from rough mutants, both of which are known to contain the toxic principle of LPS. Thus it appears that the antibodies mask the toxic regions of the LPS molecule in vivo and this enables the antibodies to protect against the lethal effects of endotoxin.

The monoclonal anti-LPS antibodies are produced by antibody-producing cell lines. The anti-LPS antibody-producing cell lines may be hybridoma cell lines commonly known as hybridomas. The hybrid cells are formed from the fusion of an anti-LPS antibody-producing cell and an immortalizing cell line, that is, a cell line which imparts long term tissue culture stability on the hybrid cell. In the formation of the hybrid cell lines, the first fusion partner—the anti-LPS antibody-producing cell—may be a spleen cell of an animal immunized against gram-negative bacteria or gram-negative bacterial endotoxin. Alternatively, the anti-LPS antibody-producing cell may be an anti-LPS generating B lymphocyte obtained from the spleen, peripheral blood, lymph nodes or other tissue. The second fusion partner—the immortal cell—may be a lymphoblastoid cell or a plasmacytoma cell such as a myeloma cell, itself an antibody-producing cell but also malignant.

Murine hybridomas which produce monoclonal anti-LPS antibodies are formed by the fusion of mouse myeloma cells and spleen cells from mice immunized against whole cell gram-negative bacteria (for example, heat inactivated E. coli J5) or isolated lipopolysaccharide from gram-negative bacteria (for example, LPS from E. coli J5). To immunize the mice, a variety of different immunization protocols may be followed. For instance mice may receive primary and boosting immunizations of whole cell gram negative bacteria. Alternatively both the primary and boosting immunogens may be lipopolysaccharide molecules or mixtures of lipopolysaccharides or the primary immunogen may be whole cell bacteria followed by LPS boosting immunogen. The fusions are accomplished by standard procedures. Kohler and Milstein, (1975) Nature (London) 256, 495-497; Kennet, R., (1980) in Monoclonal Antibodies (Kennet et al., Eds.) pp. 365-367, Plenum Press, N.Y.

The hybridomas are then screened for production of antibody reactive with whole cell gram-negative bacteria or free LPS molecules from gram-negative bacteria. Those which secrete reactive antibodies are cloned.

Human hybridomas which produce monoclonal anti-LPS antibodies are formed from the fusion of spleen cells from an individual immunized against gram-negative bacteria and a human lymphoblastoid cell line. Alternatively, the fusion partner for the myeloma cell may be a human peripheral blood antibody-producing lymphocyte sensitized against gram-negative bacteria or LPS molecules. The fusion and screening techniques are essentially the same as those used in the production and selection of murine anti-LPS generating hybridomas.

Also mouse and human hybridomas which produce human monoclonal anti-LPS antibody may be formed from the fusion of a human antibody-producing cell and a murine plasmacytoma cell. Indeed, the mouse plasmacytoma cell may be used as a fusion partner for other mammalian antibody-producing cells to form hybridomas which produce anti-LPS antibody of the particular mammal.

Another way of forming the anti-lipopolysaccharide antibody-producing cell line is by transformation of antibody-producing cells. For example, an anti-LPS antibody producing B lymphocyte obtained from an animal immunized against gram-negative bacteria or LPS, may be infected and transformed with a virus such as the Epstein-Barr virus in the case of human B lymphocytes to give an immortal anti-LPS antibody-producing cell. See, e.g., Kozbor and Roder, (1983) *Immunology Today* 4(3), 72-79. Or the B lymphocyte may be transformed by a transforming gene or transforming gene product.

The monoclonal anti-LPS antibodies are produced in large quantities by injecting anti-LPS antibody-producing hybridomas into the peritoneal cavity of mice and, after an appropriate time, harvesting the ascites fluid which contains very high titer of homogenous antibody and isolating the monoclonal anti-LPS antibodies therefrom. Xenogeneic hybridomas should be injected into irradiated or athymic nude mice. Alternatively, the antibodies may be produced by culturing anti-LPS producing cells in vitro and isolating secreted monoclonal anti-LPS antibodies from the cell culture medium.

The monoclonal anti-LPS antibodies of this invention have a number of important therapeutic uses. Foremost is the treatment of gram-negative bacteremia in mammals. The monoclonal anti-LPS antibodies are effective antimicrobial agents for combating nosocomial or endogenous gram-negative bacterial infections. The antibodies may be used in immunotherapy for protecting mammals against the lethal effects of gram-negative bacteremia and endotoxin shock. Because they confer cross-protective immunity against all important pathogenic gram-negative microorganisms, the anti-LPS antibodies are wide spectrum anti-gram negative microbial agents. Additionally the antibodies may be used in the treatment of other gram-negative bacterial infections such as urinary tract infection or in the prevention of dissemination of the microorganism from the primary site of infection into the bloodstream.

For the most effective immunotherapy it appears that combinations of anti-LPS antibodies which react with different common antigenic determinants on the LPS molecule should be administered. Further, the antibodies may be given in conjunction with antibiotics or other anti-microbial agents.

Generally the antibodies would be administered intravenously or intramuscularly in a physiologically acceptable solution.

Another important use of the anti-LPS antibodies of this invention is in prophylaxis of gram-negative bacteremia. Certain high risk groups of patients may be passively immunized against gram-negative bacteria by administering the antibodies. Such high risk groups include patients whose immune system has been suppressed or compromised such as those undergoing cancer chemotherapy, those with Acquired Immunodeficiency Syndrome (AIDS) and the aged. Other groups of patients particularly susceptible to gram-negative bacteremia are patients suffering from burns, patients with cystic fibrosis or patients undergoing surgery or other invasive procedures. In these cases, the antibody or mixture of antibodies would be administered to patients in order to bestow cross protective immunity which prevents gram-negative bacteremia. As in the treatment of bacteremia, prophylaxis of bacteremia may include the administration of antibiotics or other antimicrobial agent along with the anti-LPS antibodies.

Because of the broad cross reactivity of the monoclonal anti-LPS antibodies with gram-negative bacteria, the antibodies are useful in a variety of procedures for detecting gram-negative bacteria. The antibodies may be used to determine whether bacteria are gram-negative. For this purpose the anti-LPS antibodies may be used in a number of different immunoassays for gram-negative bacteria. These include radioimmunoassays or enzyme linked immunoadsorbent assays of the conventional types. Alternatively, the anti-LPS antibodies may be employed in fluorescence microscopy techniques for determining whether bacteria are gram-negative. In one format, the anti-LPS antibodies themselves are labeled with a fluorescent compound such as fluorescein and then brought into contact with a sample of bacteria. In an alternate format, unlabeled anti-LPS antibodies are contacted with the sample of bacteria and then a second fluorescently labeled antibody directed against the anti-LPS antibody is added. In either format binding of the anti-LPS antibodies to the bacteria can be monitored under a microscope. Finally, because there are numerous LPS antigens on the surface of gram-negative bacteria, the anti-LPS antibodies of this invention may be used in various agglutination assays or other standard immunological assays for gram-negative bacteria.

The sensitivity of each of the assays described above may be enhanced by exposing the LPS antigenic determinants on gram-negative bacteria with which the anti-LPS antibodies bind. In the case of anti-lipid A antibodies particularly, access to the antigenic determinants may be improved by pretreating the bacteria with a mildly acidic aqueous solution. This treatment preferentially removes the core and O-antigen regions of LPS. Galanos et al., (1971) *Eur. J. Biochem.* 24, 116–122.

Diagnostic kits for performance of the assays described above would include monoclonal anti-LPS antibody or labeled anti-LPS antibody or mixtures of labeled or unlabeled antibody.

The assays described above would provide physicians with a quick and reliable method of ruling out gram-negative bacteria as the etiological agent in bacteremic patients. Current gram stain techniques for determining if a clinical isolate of bacteria is gram-negative require at least a day. In order to avoid delaying treatment of an often lethal disease, usually the etiological agent is presumed to be gram-negative bacteria because gram-negative bacteria account for the majority of nosocomial bacterial infections. Consequently aminoglycosides, the chief antimicrobial agents against gram-negative bacteria, are administered. Aminoglycosides, however, cause serious toxicity, most notably ototoxicity and nephrotoxicity. Assays which would quickly rule out gram-negative bacteria as a causative agent allow physicians to avoid subjecting patients aminoglycoside therapy, and the attendant risk of serious toxicity, without any significant delay in treatment of those patients who have gram-negative bacteremia.

Because of their restricted specificity for LPS and their wide cross reactivity with LPS from different gram-negative microorganisms, the anti-LPS antibodies of this invention may be used to detect and measure gram-negative bacterial endotoxin in a biological fluid.

For this purpose, the antibodies may be used in conventional immunoassays such as radioimmunoassay or enzyme linked immunoadsorbent assay. For many of these assays an immunoadsorbent is formed by attaching anti-LPS antibody to a solid phase. In a competitive immunoassay for endotoxin, for example, a sample of the biological fluid to be assayed is contacted with the immunoadsorbent. The mixture is incubated after which a predetermined amount of labeled LPS is added. After further incubation, the immunoadsorbent with the bound LPS (that is, the LPS anti-LPS complex) is separated from the free LPS and the activity of the label in the bound or free LPS fraction is measured in order to determine the amount of endotoxin in the sample. In such assays, the label may be a radioisotope, an enzyme, or a fluorescent compound.

In addition, the anti-LPS antibodies are useful in procedures for removing gram-negative bacteria or gram-negative bacterial endotoxin from a biological fluid. One such procedure which has therapeutic value is the extracorporeal treatment of blood to remove gram-negative bacteria or endotoxin. This may be accomplished by passing the blood over a solid phase to which the anti-LPS antibody is attached. The antibody selectively binds the bacteria or endotoxin. The blood is then returned to the donor cleansed of gram-negative bacteria or endotoxin.

Analogously, the antibodies may be used to remove gram-negative bacteria or endotoxin from cell culture media. For example, the culture media from which products of naturally occurring or genetically engineered microorganisms are to be isolated are often contaminated with gram-negative bacteria or endotoxin. In a manner similar to that described for the extracorporeal treatment of blood, antibodies bound to a solid phase may be used to remove these contaminants from the media.

The anti-LPS antibodies of this invention may also be used in a number of diagnostic techniques in vivo. Labeled anti-LPS antibodies may be used in imaging techniques for localizing gram-negative bacteremic abscesses or cysts within a mammal. In such techniques the antibody is administered to a mammal suspected of having an abscess or cyst harboring gram-negative bacteria. Because of the special affinity of the antibody for gram-negative bacteria, it accumulates in the bacteremic abscess. The concentrated labeled antibody yields a detectable signal providing an image of the abscess and thereby revealing its location.

For example, the anti-LPS antibodies may be used as radiopharmaceutics in radioimmunoscintigraphy. For this purpose, the antibody is labeled with a gamma-emitting radioisotope such as $^{125}$Iodine, $^{131}$Iodine, $^{99M}$Technetium or $^{111}$Indium. A variety of methods exists for attaching radioisotopes to the antibodies either directly or via a chelating agent such as diethylene triamine pentacetic acid. Any of these procedures may be used to label the anti-LPS antibodies. Often it is preferred that an antigen binding fragment of the antibodies be used. Fab, the univalent antigen binding portion of the antibody, or F(ab')$_2$, the bivalent antigen binding portion are prepared by digesting antibody with the enzymes papain and pepsin, respectively, according to standard procedures. These antigen binding fragments are generally cleared much more quickly from the blood pool and therefore provide an abscess radio image of greater contrast within a shorter period of time.

The anti-LPS antibodies can be provided as reagents in kits for radioimmunoscintigraphy in mammals. Such kits would include the monoclonal anti-LPS antibody or fragments of the antibodies labeled with one of the gamma-emitting radioisotopes.

The anti-LPS antibodies may be used as reagents in nuclear magnetic resonance (NMR) imaging. For example the anti-LPS antibodies or antibody fragments may be labeled with a paramagnetic substance such as manganese. The labeled antibody generates a NMR active signal which yields an image of the abscess.

Two murine monoclonal anti-LPS antibodies designated 8A1 and 4A10 were deposited at the American Type Culture Collection in Rockville, Md. on Oct. 7, 1983. The antibody deposits have been assigned the following ATCC accession numbers:

8A1 ATCC #40083
4A10 ATCC #40084.

The murine hybridoma which produces the 8A1 antibody was placed on deposit on Apr. 5, 1988 at the ATCC and assigned the following accession number:

Lou25-8A1-1E1 HB 9685.

The invention will now be further illustrated with specific examples.

EXAMPLE 1

Production of Murine Monoclonal Antibodies Against Lipopolysaccharide of Gram Negative Bacteria

Preparation of Bacterial Antigens

The following lipopolysaccharides (LPS) were obtained from List Biological Laboratories, Inc. (Campbell, Calif.): *Escherichia coli* J5, *Escherichia coli* 0111:B$_4$, *Escherichia coli* 055:B$_5$ (ATCC 12014), *Klebsiella pneumoniae* (ATCC 10031), *Pseudomonas aeruginosa* FD Type I (ATCC 27312), *Salmonella minnesota* wild type (ATCC 9700), *Salmonella minnesota* R595 and *Serratia marcescens* (ATCC 14756). LPS from *Salmonella typhimurium* Re-mutant (G30-C21) was purchased from Ribi Immunochem Research, Inc. (Hamilton, Mont.). The samples were solubilized in a vendor recommended manner or all LPS samples were reconstituted in 0.5% (v/v) triethylamine (TEA), 0.9% (w/v) NaCl at 2.0 mg/ml and all further dilutions accomplished in sterile and pyrogen free phosphate buffered (30 mM, pH 7.4) saline (PBS).

*Escherichia coli* J5 is a rough mutant of *E. coli* 0111:B$_4$ which lacks the enzyme uridine diphosphate galactose-4-epimerase. Ziegler et al., (1973) *J. Immunol.* 111, 433–438. Thus, this mutant is missing the entire O-antigen side chain as well as a portion of its core structure. Both the mutant and the parent strain as well as all the other bacterial strains were provided by Dr. David Dunn (Minneapolis, Minn): *Escherichia coli* 055:B$_5$ (ATCC 12014), *Klebsiella pneumoniae* (ATCC 10031), *Pseudomonas aeruginosa* (ATCC 27312), *Salmonella minnesota*, *Salmonella minnesota* R595, *Serratia marcescens* (ATCC 14756), *Streptococcus faecalis* and *Staphylococcus aureus* (ATCC 10832). American Type Culture Collection designations are shown for those strains available.

Each organism was incubated for 18 hours in brain heart infusion (BHI) broth in a shaker bath at 37° C. and then subjected to three cycles of centrifugation at 4° C. at 3000×g for 10 minutes followed by resuspension in 0.9% (w/v) NaCl. Initial approximation of bacterial numbers was achieved using a Klett-Summerson colorimeter. Serial dilutions were performed and exact enumeration made on agar pour plates. Heat-inactivated bacterial antigen was prepared by autoclaving a log phase culture growth in BHI broth after an aliquot had been removed for enumeration.

Solid Phase radioimmunoassays (RIA)

Fifty ul aliquots of antigen solution in PBS was added to the wells of a polyvinyl u-bottom 96 well microtiter plate (Dynatech Corp., Alexandria, Va.) and left at 37° C. for 2–4 hours or overnight at 4° C. Heat inactivated whole bacterial cells were coated onto the plates at $10^8$–$10^9$ organisms per ml and the LPS variants were added to the wells at 20 ug per ml. After removing the antigen and washing 3 times with water or PBS, the wells were incubated with 200 ul of either 1% (w/v) bovine serum albumin (BSA; Sigma Chemical Co., St. Louis, Mo.), 2% or 20% (w/v) horse serum or 2% (w/v) fetal calf serum (Sterile Systems, Inc., Logan, Utah) for a minimum of 30 minutes at 37° C. and again washed 3 times. Fifty ul aliquots of hybrid supernatants or purified antibody dilutions were added to the antigen-coated wells and incubated for 2 hours at 37° C. the aliquot removed and the well washed 3 times.

Affinity purified goat anti-mouse F(ab')$_2$, or IgM (Cappel Laboratories, Inc., West Chester, Pa.), or goat anti-human IgG, IgA or IgM (Kirkegaard and Perry Laboratories, Gathersburg, Md.) which had been radiolabeled at approximately 10 uCi/ug with $^{125}$Iodine by the Iodogen (Pierce Chemical Co., Rockford, Ill.) method as described by Markwell et alk. (1978) *Biochemistry* 17, 4807–4817 were used as probes. Generally 50,000 cpm of the probe diluted in 1% (w/v) BSA-PBS was added and incubated for 2 hours at 37° C. After removing the probe and washing, the wells were cut from the plate and bound $^{125}$I determined in a gamma counter (Ne1600, Nuclear Enterprises, Edinburgh, Scotland, UK) for 1 minute.

Immunizations

Five murine anti-LPS antibodies designated 1D4, 8A1, 5E4, 6B2 and 4A10 were produced by employing the following immunization protocols.

Mouse A: 1D4. Sixteen BALB/c (Charles River Breeding Laboratories, Kingston, N.Y.) female mice were immunized on day 0, 2, 4, 7, 9, 11, 14 and 16 with an intravenous administration of $10^7$ heat-inactivated *E. coli* J5 bacteria suspended in 0.5 ml PBS. The house with the best serum titer in an RIA to both *E. coli* J5 and *S. minnesota* R595 heat-inactivated bacteria was boosted on day 23 in the same manner and sacrificed for its spleen three days later.

Mouse B: 8A1 and 5E4. Forty CAF1/J (The Jackson Laboratory, Bar Harbor, Me.) female mice were immunized with a subcutaneous (s.c.) injection of 5 ×$10^8$ heat-inactivated *E. coli* J5 bacteria in complete Freund's adjuvant. On days 7, 15, 21, 25, and 27 the mice were challenged s.c. with 2.5×$10^8$ inactivated J5 cells in incomplete Freund's adjuvant. On days 29, 36, 43, 50, 57, 64, 71 and 74 the mice were immunized with an intraperitoneal (i.p.) injection of 2.5×$10^5$ heat treated J5 bacteria in PBS. Exactly 8 weeks later the mouse which had the best anti *E. coli* J5 LPS serum titer was boosted s.c. with a mixture of 10 ug each of *E. coli* J5 LPS and *S. minnesota* R595 LPA in incomplete Fruend's adjuvant. It was sacrificed three days later.

Mouse C: 6B2. Fifty CAF1/J female mice were immunized as above for 5E4 and 8A1 except the i.p. injection ended on day 50. On day 57, the mouse with the best serum titer to *E. coli* J5 was boosted i.p. with 2.5×$10^5$ *E. coli* J5 inactive cells and sacrificed three days later. This mouse's serum showed reactivity to *E. coli* J5, *Klebsiella pneumonia*, *Pseudomonas aeruginosa* and *Serratia marcescens* heat inactivated bacteria and to *E. coli* J5 LPS.

Mouse D: 4A10. Three BALB/c female mice were immunized i.p. on day 0, 2, 4, 7, 9, 11, 14 and 16 with 25 ug *S. minnesota* R595 LPS in PBS. On day 23 the mouse with the best serum titer to Re LPS ($10^5$) was boosted i.p. with 50 ug Re LPS and three days later the mouse was sacrificed and splenectomized.

TABLE 1

Summary of Primary and Boosting Immunogens and Primary Fusion Well Screening Antigens.

| Fusion | Cell line(s) | Immunogen | Boost | Primary Fusion Screen | Wells Positive |
|---|---|---|---|---|---|
| Mouse A | 1D4 | EcJ5 WC[a] | EcJ5 WC | EcJ5 WC | 96/96[b] |
| Mouse B | 6B2 | EcJ5 WC | EcJ5 WC | EcJ5 LPS | 12/672 |
| Mouse C | 8A1 and 5E4 | EcJ5 WC | EcJ5 LPS[c] | EcJ5 LPS[c] | 5/13[d] |
| | | | SmRe LPS[e] | SmRe LPS | |
| Mouse D | 4A10 | SmRe LPS | SmRe LPS | SmRe LPS | 8/480 |

[a] Heat inactivated *E. coli* J5 bacteria.
[b] All wells were greater than 3× background.
[c] The two LPS species were mixed for boosting the mice; the fusion wells were screened on each LPS separately.
[d] 13/576 wells assayed, all showed some positive hybridoma growth but the 13 wells selected had significantly better cell proliferation and 5 were positive for both Re and J5 LPS.
[e] *S. minnesota* R595 LPS, an Re mutant.

Production of Hybrid Cells

Splenic lymphocytes from mice A, B and C were fused with NS-1 myeloma cells using a variation of standard methods first established by Kohler and Milstein, (1975) *Nature* (London) 256, 495–497. Myeloma line P$_3$x63Ag8.653 developed by Kearney et al., (1979) *J. Immunol.* 123, 1548–1550 was used as a fusion partner for mouse D spleen cells.

In general, after removal from the mouse the spleen was rinsed twice with DMEM culture medium (GIBCO, Grand Island, N.Y.) and a single cell suspension generated using a Cellector (Bellco, Vineland, N.H.) equipped with a 140 micro screen. Approximately $10^8$ spleen cells were mixed with 2×$10^7$ myeloma cells in a round bottom centrifuge tube after being rinsed 2-3 times in DMEM. After centrifugation at 183×g for 7 minutes, the supernatant was removed by aspiration and 1 ml of 30% (v/v) polyethylene glycol 1000 (PEG; Baker Chemical Co., Phillipsburg, N.J.) was added. The cell suspension was immediately centrifuged at 20-50×g for 3-4 minutes, the supernatant removed and 10 ml of HT-DMEM medium [DMEM supplemented with 15% (v/v) Hyclone fetal calf serum, 4 mM L-glutamine, 50 ug/ml Gentamycin sulfate, 13.6 ug hypoxanthine and 7.6 ug/ml thymidine] added. The cells were placed into two 100 mm petri dishes each containing 20 ml HT-DMEM and incubated at 37° C. for at least 24 hours. After being transferred into HAT-DMEM medium (HT-DMEM plus 0.18 ug/ml aminopterin), the cell suspension was distributed into 96 well microtest culture plates (Costar, Cambridge, Mass.) at 0.5-2.0×$10^5$ cells/200 ul/well and incubated at 37° C. in 8% CO$_2$. When wells having positive hybridoma growth reached approximately 50% confluency, usually within 9 to 14 days, aliquots of supernatant were removed and assayed by RIA for LPS and/or bacterial binding capacity. The results of the primary fusion screen are summarized in Table 1. Cells in the fusion plate wells of interest were immediately cloned by limiting dilution at 1 cell per well in HT-DMEM medium onto a layer of 1-2×$10^5$ BALB/c spleen cells which had been previously irradiated at 2000 rads. After several days, culture fluid from each well which had positive hybridoma growth was assayed by RIA and selected wells recloned as in the first cloning. Each well was microscopically screened a few days after cell deposition and wells containing more than one clone eliminated. Approximately 10 days later, cell supernatants were again screened by RIA and cell lines to be maintained for further study selected. Usually cell lines were weaned from HT-DMEM medium to complete DMEM medium [DMEM supplemented with 15% (v/v) Hyclone fetal calf serum, 4 mM L-glutamine and 50 ug/ml Gentamycin sulfate] at this time.

Production, Analysis and Purification of Ascites Fluids

Clones were expanded by daily passage in complete DMEM and incubated at 37° C. in 8% $CO_2$. To produce tumor ascites fluids, $5-10 \times 10^5$ cells in DMEM were inoculated intraperitoneally into syngeneic BALB/c mice which had been primed 10 to 15 days earlier by an i.p. injection of 0.5 ml Pristane (Aldrich Chemical Co., Milwaukee, Wis.). Ascites samples were taken from tumor bearing mice, pooled, centrifuged and frozen.

Pure IgG immunoglobulin fractions were isolated from ascites fluid by affinity chromatography on Protein A-Sepharose CL-4B (Pharmacia Fine Chemicals, Piscataway, N.J.) essentially as described by Ey et al., (1978) *Immunochemistry* 15, 429–436. Before application to the affinity column, the ascites was heated to 37° C. for 2 hours and then to 50° C. for an additional hour, centrifuged at $40,000 \times g$ for 45 minutes at 4° C. and 0.22 micron filtered (Millipore Corp., Bedford, Mass.).

Immunoglobulin subclass was determined on the purified ascites by immunodiffusion according to the method of Ouchterlony by using 1% (w/v) agarose (Marine Colloids, Rockland, Me.E) in PBS and specific goat antiserum to mouse IgG1, IgG2a, IgG2b and IgG3 (Gateway Immunosera Co., St. Louis, Mo.) the first three of which were affinity purified. Goat anti-mouse IgG F(ab')$_2$ was used as a positive control. These results indicated that the antibodies from clones 1D4, 8A1 and 5E4 are all of the IgG1 subclass and 6B2 is of the IgG2a subclass. Clone 4A10 showed a major precipitant line with the IgG3 antiserum and a very minor but reproducible reaction with the IgG2a reagent. The clone 4A10 secretes predominantly but perhaps not exclusively IgG3 immunoglobulins.

EXAMPLE 2

PRODUCTION OF HUMAN MONOCLONAL ANTIBODIES AGAINST LIPOPOLYSACCHARIDE OF GRAM NEGATIVE BACTERIA

Preparation of Human Mononuclear Cells

For the hybrid arising from experiment HM16A, 400 ml of blood was collected from a normal female in heparin (Sigma Chemical Co., St. Louis, Mo.). Fifty ml aliquots of blood were centrifuged at room temperature at $733 \times g$ for 20 minutes. The plasma was discarded, the buffy coat collected and diluted to 20 ml per tube with calcium and magnesium free Hanks Balanced Salt Solution containing 25 mM HEPES (HBSS; GIBCO, Grand Island, N.Y.). Each tube was underlayed with 20 ml Ficoll-Paque (Pharmacia Fine Chemical, Piscataway, N.J.) and centrifuged for 30 minutes at $733 \times g$. The mononuclear cell bands were collected, washed three times with HBSS and the cells resuspended to $1 \times 10^8$ cells/ml in RPMI 1640 (GIBCO, Grand Island, N.Y.) supplemented with 50% (v/v) heat-inactivated Hyclone fetal calf serum (FCS; Sterile Systems, Inc., Logan, Utah). To enrich for B lymphocytes the cells were then rosetted in a 30 ml Oakridge tube with freshly washed sheep red blood cells (SRBC; Hazelton Dutchland, Inc., Denver, Pa.). The SRBC were resuspended to $2 \times 10^9$ cells/ml in RPMI 1640 containing 10% (v/v) FCS and added to the mononuclear cells at a ratio of 24:1. The mixed cell suspension was centrifuged for 5 minutes at $46 \times g$, incubated on ice for 10 minutes, gently resuspended with 10 ml of the same medium, underlayed with 10 ml of Ficoll-Paque and centrifuged 30 minutes at $733 \times g$. The mononuclear cell bands were collected and washed twice.

The source of mononuclear cells for experiment HM22B was a human spleen from an *E. coli* J5 immunized donor (Dr. D. Dunn, Minneapolis, Minn.). This male patient with end stage renal disease was immunized twice intramuscularly with a ten day interval between inoculations. Each inoculum dose contained $1 \times 10^9$ heat-inactivated *E. coli* J5 whole cells. The patient was splenectomized three days after the second inoculation. The spleen was cut into $5 \times 2 \times 2$ cm pieces, treated for 15 minutes at room temperature with RPMI 1640 containing 20 ug/ml Vancomycin. The spleen was transferred to fresh RPMI 1640 supplemented with 5% (v/v) FCS, 25 mM HEPES and 50 ug/ml Gentamycin sulfate, minced to $1 \times 2 \times 2$ cm pieces and transported on ice. Spleen cells were obtained by a combination of sieving through bags made from Nitex bolting cloth (Tobler, Ernst, and Traber, Elmsford, N.Y.) and mincing. Part of the resultant single cell suspension was used fresh for experiment HM22B. The excess cells were frozen in RPMI 1640 containing 20% (v/v) FCS and 10% (v/v) dimethyl sulfoxide. The mononuclear cells for HM22B were separated on Ficoll-Paque and washed. The cells in HM16A were fused immediately. Those in HM22B were cultured for 5 days $1 \times 10^6$ cells/ml at 37° C. in 5% $CO_2$ in RPMI 1640 supplemented with 10% (v/v) FCS, 4 mM L-glutamine, 50 ug/ml Gentamycin, 0.1% (v/v) pokeweed mitogen (GIBCO, Grand Island, N.Y.), 7.6 ug/ml thymidine and 13.6 ug/ml hypoxanthine.

Fusions

Mononuclear cells were washed two times in RPMI 1640. An equal number of WI-L2-729-HF2- cells, hereafter called-HF2, were also washed twice in RPMI 1640. This human lymphoblastoid, which is resistant to 6-thioguanine, was selected for its good fusion partner characteristics. (Dr. R. Lundak, Riverside, Calif.) The cells were resuspended in RPMI 1640, mixed in a 30 ml Oakridge tube, pelleted and the supernatant removed. The cells were agitated to break up the pellet. Four 0.25 ml aliquots of 35% (v/v) PEG in RPMI 1640 were added at 15 second intervals while the cells were agitated. The mixture was centrifuged 3 minutes at $46 \times g$ and the PEG removed. The cells were gently resuspended in complete RPMI 1640 [RPMI 1640 supplemented with 10% (v/v) FCS, 4 mM L-glutamine, and 50 ug/ml Gentamycin sulfate] to a concentration of $2 \times 10^6$ HF2 cells/ml and cultured overnight. The following day the cells were pelleted, resuspended to $5 \times 10^5$ HF2 cells/ml in HAT-RPMI 1640 (RPMI 1640 containing 6.8 ug/ml hypoxanthine, 0.18 ug/ml aminopterin and 3.8 ug/ml thymidine). The cells were plated at 1 ml per well in 24 well cluster dishes (Costar, Cambridge, Mass.) containing MRC-5 human embryo lung fibroblasts (Dr. J. P. Jacobs, London, England) as a feeder layer.

This feeder layer was prepared as follows. Confluent monolayers of the MRC-5 cells were cultured in T-75 tissue culture flasks (Costar, Cambridge, Mass.) in MEM medium (GIBCO, Grand Island, N.Y.) containing 10% (v/v) FCS and 4 mM L-glutamine. The medium was replaced with 0.02% (w/v) sodium ethylene diamine tetraacetate in PBS and the cells detached with 0.025% (w/v) trypsin (GIBCO, Grand Island, N.Y.). The detached MRC-5 cells were seeded at 25% of the original density into the 24 well cluster dishes as the feeder layer.

For the next four days after the fused cells were deposited on the feeder layers, 0.5 ml HAT-RPMI 1640 medium was removed and replaced with medium containing twice the above concentrations of hypoxanthine, aminopterin and thymidine. Thereafter the cultures were refed weekly.

Screening

Culture supernatants were screened by solid phase radioimmunoassay (RIA) about one week after the appearance of hybridomas. The assay was performed as described in Example 1; $10^8$ heat-inactivated *E. coli* J5 cells per ml was used as the well coating antigen.

Plates which did not receive *E. coli* J5 but were only blocked with 2% (v/v) horse serum served as controls. Wells were considered to be positive for antibody if more than 1000 cpm were bound on *E. coli* J5 and the background was less than half the cpm bound. Background is defined as cpms bound to control wells.

Cloning

Hybridomas from wells with antibody were first cloned by limiting dilution in 96 well cluster dishes. Serial 10 fold dilutions of hybridoma cells were seeded in the 96 well cluster dishes containing 70-80% confluent, 2000 rad irradiated MRC-5 cells. Each dilution was monitored for the frequency of wells positive for hybridoma growth and the frequency of wells with hybridoma cells positive for antibody by RIA.

In the first clonings after hybridization, the limiting dilution for hybridoma growth was generally $10^{-3}$, while the limiting dilution for detectable antibody secretion was the $10^{-1}$ or $10^{-2}$ dilution of hybridoma cells. Subsequent clonings required fewer cells per well to give hybridoma growth and antibody production. When all of the wells at the limiting dilution for hybridoma growth were also positive for antibody secretion, those hybridoma cells showing maximum reactivity in their supernatants by RIA were cloned at 10 and 1 cells per well. Antibody positive cells were detected as above.

After cloning the hybridoma cells were routinely propagated in growth medium by adjusting the cell density to $1 \times 10^5$ cells per ml twice a week. Periodically 3 to 4 day supernatants were assayed by RIA to monitor continued antibody production. Antibody secretion was maintained after 13 to 21 months in culture.

Characterization of the Human Monoclonal Anti-LPS Antibodies

For class typing of the human monoclonal antibodies, tissue culture supernatants from each of the cell lines were serially two-fold diluted in 1% (w/v) BSA-PBS and examined in an RIA using heat-inactivated *E. coli* J5 organisms as coating antigen and radiolabeled goat anti-human IgG or IgM as a probe. Supernatant from the cell line HF2 was used as negative control. As seen in Table 3, both human hybridoma cell lines secrete human antibody of the IgM class which are specific for *E. coli* J5 organisms.

In order to quantitate total human IgG and IgM secretion, RIA's were performed where goat anti-human IgM or IgG was coated on the polyvinyl plate instead of bacterial antigen and cell supernatants and probe added in the usual manner. A concentration calibration curve was constructed using quantitative human IgM and IgG standards (Meloy, Springfield, Va.). The following secretion rates were established; 2.2 ug/$10^6$ HM16A cells/24 h and 0.1 ug/$10^6$ HM22B cells/24 h. Maximal IgM accumulation was usually at 5-6 days; typically HM16A was 5 ug/ml and HM22B was 0.3 ug/ml. There was no IgG secretion by either cell line as measured in this assay.

TABLE 2

| | Human Cell Fusion Frequency. | |
|---|---|---|
| Cell Line | % Positive Hybrids[a] | % Positive Secretory[b] |
| HM16A | 100(320/320) | 3(10/320) |
| HM22B | 92(133/144) | 4(5/133) |

[a]% of the wells positive for hybrid cell growth; actual numbers in parentheses.
[b]% of the wells containing hybrid growth which are also positive for antibody secretion; heat-inactivated *E. coli* J5 organisms were used as antigens in the screen.

TABLE 3

| | Human Antibody Class Characterizations. | |
|---|---|---|
| | Anti human IgG | Anti-human IgM |
| Cell Line[a] | (cpms bound) | |
| HM16A | 546 | 11832 |
| HM22B | 624 | 11968 |
| HF2[b] | 276 | 600 |

[a]Cell supernatants were assayed directly and verified with titer; heat-inactivated *E. coli* J5 organisms were used as coating antigen.
[b]Supernatants from cell line HF2 provided the negative control.

EXAMPLE 3

Bacterial Whole Cell Binding Studies

Murine anti-LPS antibodies

Several gram-negative organisms were screened in a RIA for binding to the murine monoclonal anti-LPS antibodies described in Example 1. In this assay, heat-inactivated whole organisms were coated at $5 \times 10^7$ cell/well into 96 well microtiter plates, 10, 1 or 0.1 ug aliquots of the purified monoclonals (except for 6B2) were added to each well and positive binding observed by development with $^{125}$I labeled goat anti-mouse IgG F (ab')$_2$ immunoglobulin (50,000 cpm/well). The same assay was performed with monoclonal R11D10, an anti-myosin antibody (Dr. J. Mattis, West Chester, Pa.). This antibody served as a negative control. Binding of any monoclonal antibody to the various bacteria was defined as positive when the signal was twice that of the negative control. Table 4 summarizes the results of these experiments.

Three of the murine-monoclonal anti-LPS antibodies exhibited distinct reactivity to every gram-negative organism against which screened and no reactivity to either-gram-positive bacteria tested One monoclonal, 4A10, also exhibited binding to the entire panel of gram-negative bacteria. However, it also showed a weakly positive binding (2.2 and 2.1 times the negative control respectively) to both gram-positive organisms. Because this antibody consistently has higher non-specific binding to the plate than either the negative control or the other four murine anti-LPS antibodies, this result is considered artifactual and binding in shown as ± in Table 4 for the two gram-positive strains. This conclusion is further supported by the fact that 4A10 has an average and minimum binding to the gram-negative organisms of 5.1 and 2.9 times the negative control respectively. Finally, clone 6B2 cell supernatants exhibited positive binding to all but one strain of gram-negative organisms checked and no reactivity with the gram-positive organisms.

These results are significant because they demonstrated that the anti-LPS monoclonal antibodies bind to gram-negative bacteria from distinct genera and more importantly genera of pathogenic significance.

TABLE 4

Binding of Murine anti-LPS Antibodies to Heat-Inactivated Bacteria by RIA.

| Bacteria[a] | Monoclonal anti-LPS antibody[b] | | | | |
|---|---|---|---|---|---|
| | 1D4 | 5E4 | 8A1 | 4A10 | 6B2[c] |
| Gram Negative | | | | | |
| Escherichia coli J5 | + | + | + | + | + |
| Salmonella minnesota R595 | + | + | + | + | + |
| Salmonella minnesota | + | + | + | + | nd[d] |
| Escherichia coli 0111:B4 | + | + | + | + | + |
| Escherichia coli O55:B5 | + | + | + | + | nd |
| Klebsiella pneumonia | ++ | ++ | ++ | ++ | + |
| Pseudomonas aeruginosa | ++ | ++ | ++ | ++ | − |
| Serratia marcescens | + | + | + | + | + |
| Gram Positive | | | | | |
| Staphlococcus aureus | − | − | − | ±[e] | − |
| Streptococcus faecalis | − | − | − | ± | − |

Scale defined relative to negative control, all values are the average of duplicate assays: −, less than 2×; +, 2× to 6×; ++, greater than 6×.
[a]Coated with 50 ul of $10^9$ organisms per ml PBS; blocked with 2% (v/v) fetal calf serum.
[b]Incubated at 1 ug per 50 ml PBS for 2 hours
[c]Data is from an earlier screening experiment; in this case tissue culture hybridoma cell supernatants were used.
[d]Not determined.
[e]4A10 consistently shows higher backgrounds than the negative control; thus, this signal is judged an artifact; see text for details.

Human Anti-LPS Antibodies

Supernatants from the two human anti-LPS cell lines were screened against the same panel of bacteria as above. In this assay, the organisms were coated at $5 \times 10^6$ cells/well and aliquots of serial two-fold diluted human hybridoma cell supernatants were added. All dilutions were performed in PBS. Binding was observed by the addition of $^{125}$I-labeled goat anti-human IgM immunoglobulin at 50,000 cpm/well. Supernatant from the fusion partner cell line HF2 was used as a negative control. Binding of a human monoclonal to a bacteria is defined as positive when the signal is four times that of the negative control. Table 5 summarizes the results of the experiments performed on undiluted cell supernatants. In every case, positive binding was verified by serial dilution.

One of the human monoclonal antibodies, HM16A, reacted with every gram-negative organism screened. The other antibody, HM22B, showed positive reactivity against several, but not all-gram-negative bacteria. Neither of the human monoclonal anti-LPS antibodies showed any binding to either of the gram-positive organisms. The HM16A cell supernatants routinely accumulated 2–5 ug/ml of antibody, yet the HM22B supernatants typically secreted only 0.1–0.3 ug/ml of the human IgM. The fact that the HM22B supernatant did not show positive reactivity with every gram-negative organism may be a result of the significantly lower concentration of specific antibody.

As with the murine anti-LPS antibodies, the results are significant because they demonstrate that human anti-LPS antibodies, HM16A and HM22B both bind to gram-negative bacteria from distinct genera.

TABLE 5

Binding of Human Anti-LPS Antibodies To Heat-Inactivated Bacteria by RIA.

| Bacteria | Monoclonal human antibody[b] | |
|---|---|---|
| | HM16A | HM22B |
| Gram Negative | | |
| Escherichia coli J5 | ++ | + |
| Salmonella minnesota R595 | ++ | ++ |
| Salmonella minnesota | ++ | ++ |
| Escherichia coli 0111:B4 | ++ | − |
| Escherichia coli O55:B5 | ++ | − |
| Klebsiella pneumonia | ++ | − |
| Pseudomonas aeruginosa | ++ | + |
| Serratia marcescens | ++ | − |
| Gram Positive | | |
| Staphloccus aureus | − | − |
| Streptococcus faecalis | − | − |

Scale defined relative to negative control (supernatants from the fusion partner cell line): −, less than 4×; +, 4 to 10×; ++, greater than 10×.
[a]Coated with 50 ul of $10^8$ organisms per ml PBS; blocked with 2% fetal calf serum
[b]Incubated with 50 ul cell supernatant for 2 hours

EXAMPLE 4

LPS Binding Studies by RIA

Determinant Localization for Murine Anti-LPS Antibodies

The purified and $^{125}$I labeled monoclonal anti-LPS antibodies were screened in a direct binding RIA against several smooth (wild type) and rough (mutant lacking O-specific polysaccharide) LPS variants. In these direct binding experiments, constant amounts of radiolabeled antibody were added to 96 well micro-titer plates which had been coated at serial ten fold dilutions of LPS. Initial experiments were done on lipopolysaccharides which had been reconstituted in a vendor-recommended manner at concentrations ranging from 10 ug to 1 pg per well. The data from these experiments showed that there are distinct differences among the various antibodies in their binding to rough lipopolysaccharides and to free lipid A and none of the anti-LPS antibodies could bind to any smooth LPS tested in this assay format. Preliminary attempts to allow antibody binding by dispersing the O-specific polysaccharide containing LPS variants with methanol, ionic and nonionic detergents or EDTA were unsuccessful. This implies that in the solid phase form of LPS, access to the core region is sterically hindered by the O chain polysaccharide region.

The experiments were repeated on E. coli J5 LPS, S. minnesota R595 LPS and on free lipid A derived from S. minnesota R595 LPS. In this case, all antibodies were purified under sterile-pyrogen free conditions, radiolabeled and used within three weeks. The LPS samples were dispersed on 0.5% (v/v) TEA, 0.9% (w/v) NaCl (sterile and pyrogen free) and also were used within three weeks of reconstitution. These precautions were taken to minimize any counter-ion (aggregation state) or age differences in the LPS samples.

Figure 2:
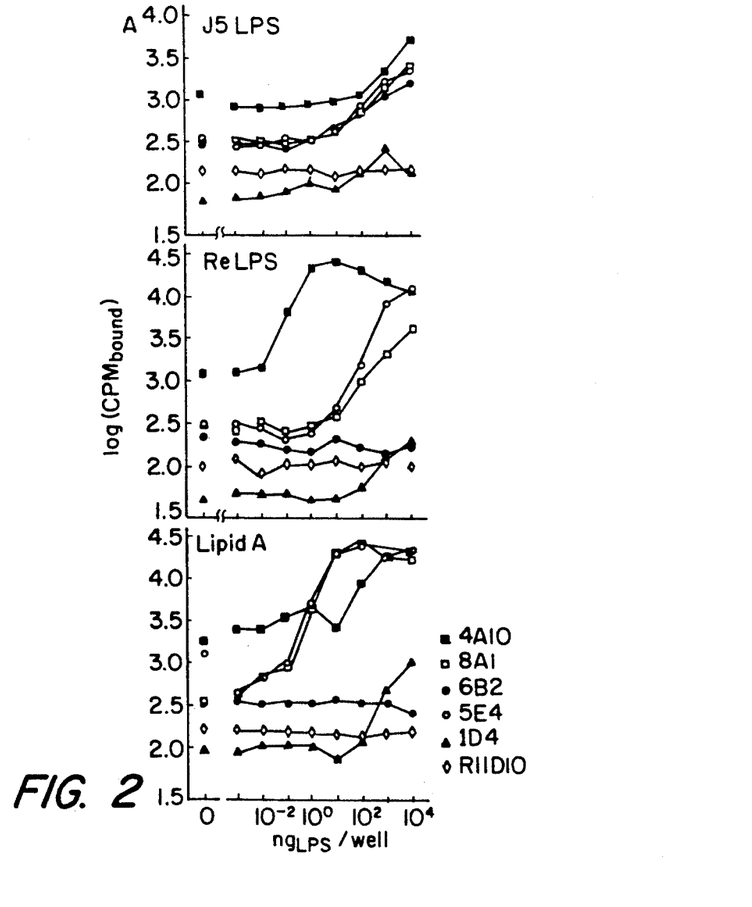
FIG. 2 shows antigen dilution curves for the murine monoclonal anti-LPS antibody against E. coli J5 LPS (FIG. 2A), S. minn. Re LPS (FIG. 2B) and free lipid A (FIG. 2C) as measured by radioimmunoassay (RIA).

The results of the binding of six monoclonal antibodies (five anti-LPS and one negative control) to E. coli J5 LPS, to S. minnesota R595 LPS and to free lipid A are shown in FIG. 2. All five of the anti-LPS monoclonal antibodies exhibited similar binding patterns to E. coli J5

LPS at high antigen levels (i.e. high concentrations of LPS used to coat the plate) and had little or no binding at low LPS concentrations (FIG. 2A). These results essentially reproduced the findings of the original experiments. The only difference is that 6B2 in the original screen exhibited both binding at lower antigen concentrations ($10^0$ ug/well) and higher maximal CPM bound (approximately 2 fold) at high LPS coating levels. This may have been a result of the different reconstitution buffer. Regardless, the difference does not effect any interpretations. For S. minnesota R595LPS (FIG. 2B), 4A10 exhibited the best binding in terms of titer, 8A1 and 5E4 had similar intermediate binding, 1D4 exhibited low levels of binding at high Re LPS coating concentrations and 6B2 had no significant binding. Again this agreed with the original experiment except that 6B2 dropped from a weak binder to a non-binder for Re LPS and 1D4 appeared to have weaker maximal levels of binding than the original results indicated. Finally, as shown in FIG. 2C, 5E4 and 8A1 had nearly identical high titer binding for free lipid A, 4A10 and 1D4 have apparently intermediate titers and 6B2 demonstrated no binding capacity at all in accord with the original screen.

In general, the antibodies displayed very different background levels (0 ug/well in FIG. 2). Consistently, 4A10 had very high and variable backgrounds but 1D4 was extremely low and highly reproducible. This statement is true for several lots of radiolabeled antibodies under slightly different assay conditions. The use of a negative control R11D10, an IgG2a antibody, demonstrated that under the conditions of this assay, there was no appreciable non-specific binding of murine monoclonal anti-LPS antibodies to any of the LPS variants tested.

The results of these binding studies indicated that monoclonals 1D4, 4A10, 8A1 and 5E4 recognized determinants which are accessible in E. coli J5 LPS, S. minnesota R595 LPS and free lipid A. In this group, 8A1, 5E4 and 1D4 had both maximal binding to and highest sensitivity in detecting free lipid A on the microtiter plates. This strongly implies that their respective binding sites reside in the lipid A portion of the lipopolysaccharide molecule. Monoclonal 4A10 demonstrated strongest binding to Re LPS. The fact that 4A10 also bound somewhat to free lipid A derived from the Re LPS suggests the determinant includes portions of the KDO region and the lipid A (see FIG. 1B). Alternatively the determinant may reside completely in the lipid A portion of Re LPS but is partially destroyed in the chemical generation of free lipid A. Finally, 6B2 showed binding only to J5 LPS. This suggests that the binding could reside in the "heptose" portion of the core of J5 LPS (see FIG. 1B). In the preliminary experiments, 6B2 also bound to S. typhimurium Re LPS. Thus the localization of binding for 6B2 to J5 LPS is equivocal. It is clear that 6B2 does not bind to S. minnesota R595 LPS nor free lipid A derived from the Re LPS under the conditions utilized to generate FIG. 2.

Human Anti-LPS Antibodies

Supernatants from the two human cell lines, HM16A and HM22B, were screened for their ability to bind to LPS. In this experiment LPS was coated into microtiter plate wells at 1 ug/50 ul PBS as described in Example 1. As in the bacterial whole cell binding studies radiolabeled goat anti-human IgM as a probe for positive binding and HF2 cell supernatant acted as a negative control. The two human cell line supernatants were independently screened against LPS from the following organisms: E. coli J5, E. coli 0111:B4, E. coli 055:B5, S. minnesota R595 and lipid A prepared from S. minnesota R595 LPS.

The HM16A tissue culture supernatants could not bind to any LPS tested in this assay format. However, HM22B-cell supernatants were found to show substantial—greater than 20 times background—binding to and only to Re LPS. These experiments demonstrate that the cross reactivity of HM22B antibody to the four bacteria shown in Table 5 is due to an anti-LPS specificity. On the other hand, HM16A could not be shown to be anti-LPS in this RIA.

Figure 1:
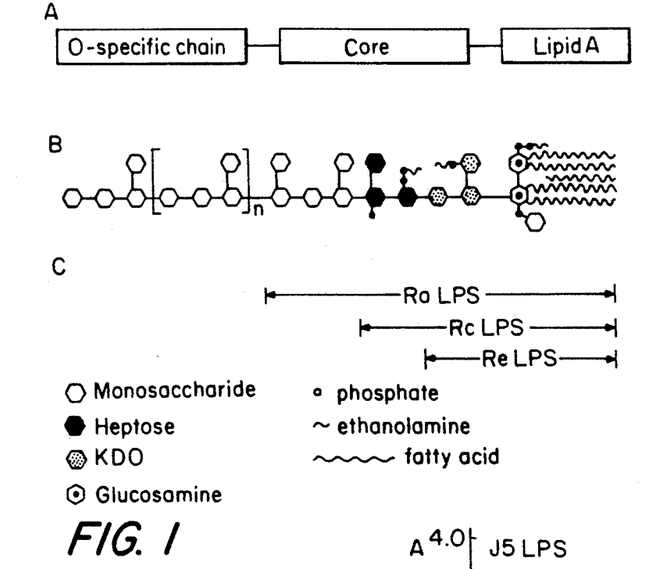
FIG. 1 summarizes the major structural features of lipopolysaccharide, the endotoxin of gram-negative bacteria. It includes a block diagram of the antigenic regions of LPS (FIG. 1A), a schematic representation of Salmonella LPS (FIG. 1B), and it indicates the position of carbohydrate chain termination for three rough mutant chemotypes of Salmonella LPS (FIG. 1C).

The fact that HM22B reacts with S. minnesota R595 LPS and not to lipid A chemically prepared from this ReLPS suggests that HM22B recognizes a determinant in the KDO region of the LPS (see FIG. 1). The same caveats discussed above for the murine anti-LPS antibody 4A10 apply here to HM22B.

EXAMPLE 5

LPS Binding Studies by an Immunoblotting Assay

Since the murine monoclonal antibodies were not able to bind to LPS isolated from smooth or wild type gram-negative bacteria absorbed to a solid-phase in the RIA format, a different binding assay was developed.

Gel Electrophoresis and Electrotransfer of LPS to Nitrocellulose

The various LPS samples were subjected to polyacrylamide gel electrophoresis (PAGE) in the presence of sodium dodecyl sulfate (SDS) and urea; the samples were then visualized using a silver staining technique. These methods have been described by Tsai et al., (1982) Anal. Biochem. 119, 115–119. The slab was comprised of a 3% (w/v) stacking gel and a 14% (w/v) running gel with a typical load of 10 ug of LPS per lane. A constant current of 5–10 ma/gel slab was used until the indicator dye entered the running gel at which time the current was adjusted to 35 ma/gel slab.

Figure 3A:
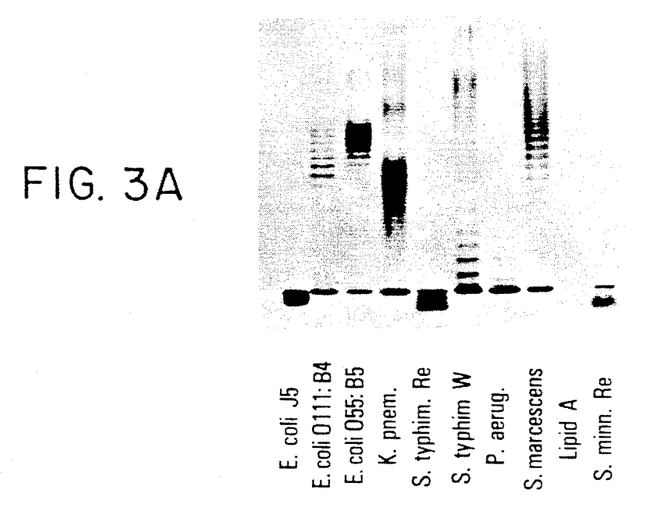
FIG. 3 illustrates the results of immunoblot assays to detect the binding of monoclonal antibody 8A1 on a silver stained gel (FIG. 3A), a typical assay gel (FIG. 3B) and with a double load of 5 LPS variants and overexposure of the film (FIG. 3C).

In this SDS-PAGE system, the LPS samples are resolved into a series of components. Each band represents an individual molecular species; the slower moving bands having larger O chain regions and the fastest moving bands having small or no O specific carbohydrate side chain. Ten different LPS samples were analyzed in this system (FIG. 3A). It is readily apparent that the amount and distribution of high molecular weight LPS components varies markedly from species to species. However, all the LPS samples except for free lipid A have components of similar low molecular weight which can be visualized with the silver staining technique.

A procedure for electrophoretic transfer of LPS from the polyacrylamide gel to nitrocellulose sheets was developed. Similar procedures for protein transfer have been described by Towbin et al., (1979) Proc. Natl. Acad. Sci. USA 76, 4350–4354. The electroblotting of LPS from the SDS gel to 0.45 um nitrocellulose paper (Schleicher and Schuell, Inc., Keene, N.H.) was performed using a Transphor electrophoretic transfer unit (Hoefer Scientific Instruments, San Francisco, Calif.). Briefly, a piece of nitrocellulose, presoaked in transfer buffer containing 24 mM Tris, 192 mM glycine, 20% (v/v) methanol at pH 8.3 was carefully placed onto the gel. This was then sandwiched between two pieces of Whatman 3 MM paper previously saturated with transfer buffer and placed into the apparatus with the gel toward the cathode and the nitrocellulose toward the anode. The LPS was transblotted to the nitrocellulose at 5 ma constant current per gel slab overnight at room temperature. This low current density was found to be necessary for efficient transfer.

Immunological Detection of LPS on Nitrocellulose

The LPS containing blots were soaked in 1% (w/v) BSA-PBS for 30 minutes at room temperature in order to block protein binding sites on the nitrocellulose. Enough monoclonal antibody in PBS was added to bring the final concentration to 10 ug/ml and the transblot was gently agitated for 3 hours. After extensive washing in PBS, the nitrocellulose sheet was incubated with 100 ml of $^{125}$I-labeled goat anti-mouse IgG F(ab')$_2$ or $^{125}$I-labeled goat anti-human IgM probe for 2-3 hours at room temperature. The radiolabeled probe was prepared as described in Example 1 at a specific activity of approximately 10 uCi/ug and used at $10^5$ cpm/ml in 1% (w/v) BSA-PBS buffer. The electrophoretic blot was exhaustively washed in PBS and thoroughly dried with a heat gun. The blots were exposed to Kodak X-Omat AR film (XAR-5; Eastman Kodak Co., Rochester, N.Y.) using a Dupont Lightning Plus intensifying screen (Picker International, Highland Heights, Ohio).

Murine Anti-LPS Antibodies

Figure 3B:
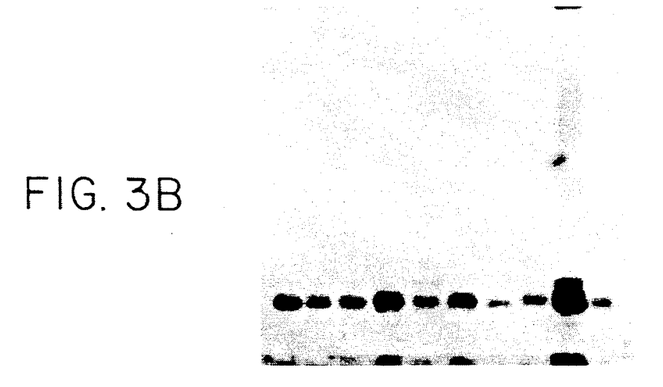
Figure 3C:
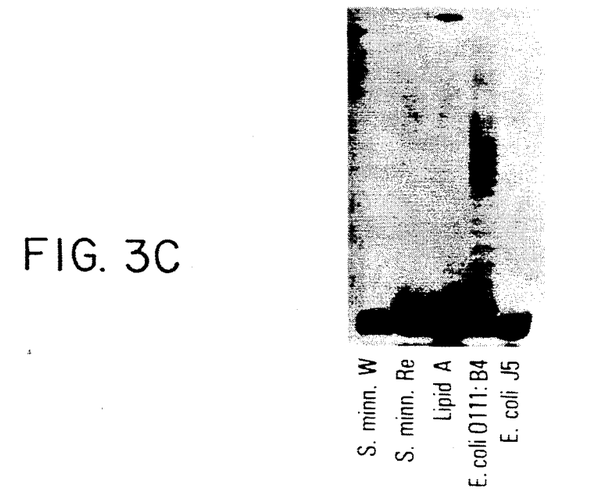

Two of the affinity purified monoclonal antibodies, 8A1 and 4A10 were screened for LPS binding in this SDS-PAGE immunoblot assay. Both showed positive reactivity to LPS from smooth organisms. This contrasts the results of the LPS binding studies in the RIA. A typical assay with 8A1 is shown in FIG. 3B. A point that is immediately evident when one compares the silver stained gel (FIG. 3A) with the immunological detection (FIG. 3B), is that 8A1 preferentially binds to the small molecular weight components of all the LPS variants screened. In order to find out if the monoclonal 8A1 exclusively bound to the fast moving bands, the experiment was repeated using a double load of 5 LPS variants and overexposing the film (FIG. 3C). Here, weak binding is seen to all of the components in the *E. coli* 0111:B$_4$ LPS but not to the *S. minnesota* wild-type LPS.

Transblotting efficiency was checked in two ways. First, in order to show that all LPS species migrated from the polyacrylamide gel during transblotting, two gels were run under identical conditions. One was silver stained directly and the second was transblotted and then the gel was silver stained. All bands were visible in the transblotted gel, but all at substantially diminished intensity relative to the control gel. Although this method is not absolutely quantitative, this data emphatically suggests that there was no selective migration of certain LPS components from the gel. Second, a *E. coli* 0.111:B$_4$ specific monoclonal antibody, 5B10, was developed. In an immunoblot assay run identically to that above, this antibody strongly reacts with all the *E. coli* 0111:B$_4$ LPS components. Thus, all the LPS components of *E. coli* 0111:B$_4$ LPS bind to the nitrocellulose sheet and the very different immunostaining intensity between high and low molecular weight components is not a result of differential transfer of those components to nitrocellulose. The conclusion is that 8A1 does bind preferentially but not exclusively to the small molecular weight components in all the LPS samples including preparations from smooth type organisms.

The two murine monoclonals tested in the immunoblot assay did show differential activities. Antibody 8A1 reacted most strongly with free lipid A components which were not detectable by silver staining (FIGS. 3A and 3B). This reinforces the conclusion that 8A1 is an anti-lipid A monoclonal antibody. Monoclonal 4A10, in agreement with the RIA results in Example 4, exhibited the most intense binding with *S. minnesota* Re LPS.

Comparison of RIA and SDS-PAGE Immunoblotting Assays

The RIA and immunoblot assays taken in aggregate prove conclusively that the broad cross-reactivity of the human (HM22B) and murine (8A1, 5E4, 4A10, 1D4 and 6B2) monoclonal antibodies is because of their anti-LPA specificity. It may well be that the bulk of the whole cell cross-reactivity is due to the interaction of the anti-LPS antibodies with LPS components on the surface of the organism which have either small O-specific side chains or no O-chain altogether. The lack of binding to LPS from smooth (O-specific polysaccharide containing) gram-negative bacteria in the RIA assay format suggests that, on the polyvinyl plate, LPS exists as an aggregate in which those LPS components having large carbohydrate side-chains sterically hinder access of antibody to the small molecular weight components.

The most significant fact remains that above mentioned human and murine monoclonals have an anti-LPS activity.

EXAMPLE 6

Screening of Anti-LPS Antibodies Against Crude Outer Membranes from *Pseudomonas Aeruginosa*

Murine monoclonal anti-LPS antibodies 8A1 and 5E4 were screened against a panel of crude outer membranes from various strains of *Pseudomonas aeruginosa* using methods similar to those described in Example 5. Outer membranes were from a set of strains representing the 17 serogroups recently defined by Liu et alk. (1983) *Int. J. Syst. Bacteriol.* 33, 256-264, and from *P. aeruginosa* PA01 strain H103. The specific strains, growth conditions and outer membrane techniques are described in Hancock et alk. (1982) *Infect. Immun.* 37, 167-171. Another set of outer membranes prepared from 14 different mucoid isolates from human cystic fibrosis patients was provided by Dr. Robert Hancock (Vancouver, British Columbia).

Figure 4A:
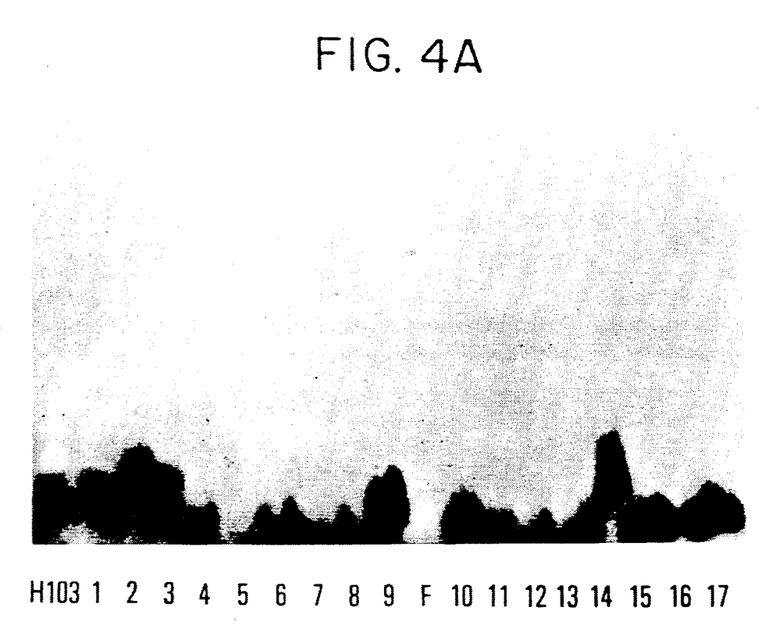
FIG. 4 shows the binding of the murine monoclonal anti-LPS antibody 5E4 with 17 serotypes of P. aeruginosa, each serotype representing a chemically distinct LPS O-specific polysaccharide.

In FIG. 4A, the results of the immuno-enzyme staining with monoclonal 5E4 for the 17 serotype specific strains and for *P. aeruginosa* PA01 strain H103 are shown; the lane marked F is a protein negative control. As in Example 5, the anti-LPS antibody preferentially bound to the lower molecular weight LPS component. Furthermore, the different mobilities of the immuno-stained components implies that structural differences exist between these LPS components in the various strains. However, these differences do not preclude antibody binding.

Figure 4B:
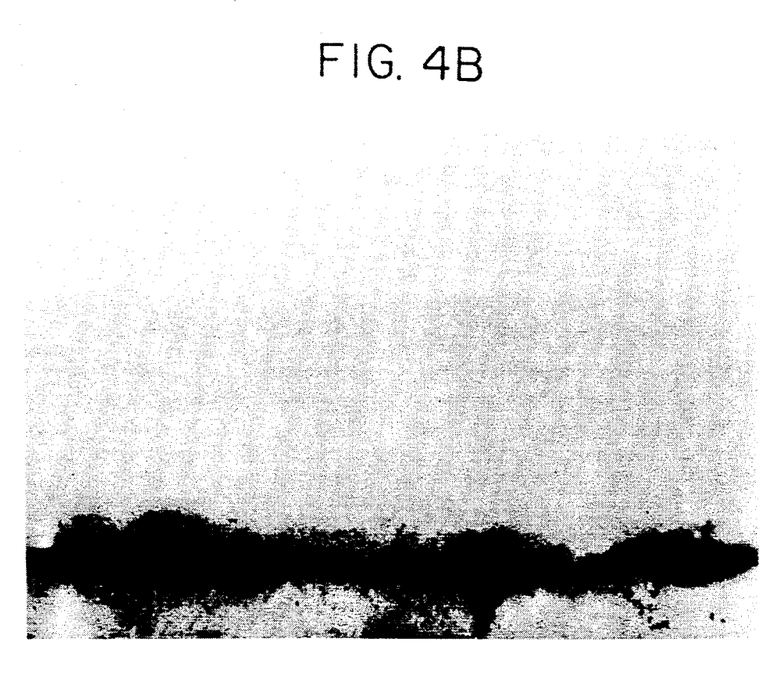

The same assay was performed against crude outer membrane preparations of 14 *P. aeruginosa* isolates from cystic fibrosis patients. Again, 8A1 and 5E4 anti-LPS antibodies bound to the rough-type LPS present in all of these serologically unclassified strains. The results for 8A1 are shown in FIG. 4B.

Thus monoclonal antibodies derived from *E. coli* immunized mice recognize LPS from serologically distinct strains of *P. aeruginosa* and from serologically unclassified natural isolates. This indicates that both 8A1 and 5E4 recognize an antigenic determinant within the lipopolysaccharide molecule which is highly likely to be conserved in new unclassified strains of *P. aeruginosa*.

EXAMPLE 7

Passive Immunization

The efficacy of several of the murine anti-LPS monoclonal antibodies as immunotherapeutic agents was tested in several model systems using mice.

Direct Sepsis Model

In this model, mice first received an intraperitoneal inoculation of a murine anti-LPS monoclonal antibody mixture at several concentrations and were subsequently infected intravenously 16–24 hours later with a 2-3LD$_{50}$ dose of one of three challenge bacteria. The lethal dose curves had been established by prior experiment and bacteria were cultured and quantified as described in Example 1. This model is similar to that described by Dunn et al., (1982) *Surgery* 92, 212–219, for guinea pigs except that physiological monitoring was omitted and efficacy was established by protection from death. The antibody used in these experiments was an equimolar mixture of anti-LPA monoclonals 8A1, 5E4, 6B2 and 1D4. The anti-myosin monoclonal R11D10 as well as physiological saline were both used as negative controls.

As can be seen in Table 7, all mice receiving negative control antibody or saline died, while the anti-LPS mixture of antibodies elicited significant protection from death in an antibody dose dependent fashion. Therefore a mixture of monoclonal antibodies in which *E. coli* J5 had been used as an immunogen can protect mice subsequently infected with *E. coli* J5, or its parental wild-type strain *E. coli* 0111:B$_4$. But most importantly, the anti-LPS antibodies can protect mice from a lethal challenge of *Klebsiella pneumoniae*, a bacterial strain from a different genus than *E. coli*. Thus, the broad cross reactivity of these antibodies demonstrated in vitro can also be maintained in vivo.

TABLE 7

| Challenge Organism[a] | Survival of Mice Seven Days After Intravenous Bacterial Challenge. | | | | | | |
|---|---|---|---|---|---|---|---|
| | Anti-LPS[b] | | | Anti-Myosin[c] | | | |
| | 1 mg | 4 mg | 8 mg | 1 mg | 4 mg | 8 mg | Saline |
| | % Survival[d] | | | | | | |
| *E. coli* J5 | nd[e] | 80[f] | 83[f] | nd | 0 | 0 | 0 |
| *E. coli* 0111:B$_4$ | 10 | 20 | 80[f] | 0 | 0 | 0 | 0 |
| *K. pneumoniae* | nd | nd | 83[f] | nd | nd | 0 | 0 |

[a]Dose of 2-3 times LD$_{50}$.
[b]Equimolar mixture of anti-LPS monoclonal antibodies 8A1, 5E4, 1D4 and 6B2.
[c]R11D10, described in Example 3.
[d]10-12 mice per group.
[e]Not determined.
[f]Data is statistically different from controls at the 99% confidence level.

Burn Wound Sepsis Model

One of the anti-LPS monoclonal antibodies was tested in a burn wound sepsis model as described by Cryz et al., (1983) *Infect. Immun.* 39, 1072–1079, in which an extremely virulent human pathogen, *Pseudomonas aeruginosa* PA220 (Dr. S. Cryz, Berne, Switzerland) was used as a challenge organism.

The animals, 18–20 g Swiss Webster out-bred mice, were anesthetized in an atmosphere of methoxyfluorane (Penthrane: Abbott Laboratories, North Chicago, Ill.) The mice were then subjected to a 10 second ethanol burn over a 2 cm$^2$ area of the back. The challenge organism was immediately injected subcutaneously into the wound. Mice received a passive transfer of monoclonal antibody intravenously at specified times before and after bacterial challenge. Control mice receiving the burn and PBS only, routinely survived.

Since the anti-LPS monoclonal used, 8A1, is of the IgG1 subclass of mouse immunoglobulins, a matching subclass monoclonal antibody was used for the negative control. The specificity of the negative control is for Hepatitis B Surface Antigen (HBsAg) and it is an IgG1 monoclonal antibody (Dr. V. Zurawski, West Chester, Pa.).

Anti-LPS monoclonal antibody 8A1 and the anti-HBsAg control monoclonal were given to separate groups of mice 24 hours before infection. Another group of mice received 8A1 both 24 hours before and 20 hours after infection. Although the absolute mortality of mice was not appreciably different, the death of mice in both groups treated with monoclonal 8A1 was significantly delayed (Table 8). Perhaps of greater significance was the relative condition of the mice after the challenge. The mice receiving two doses of 8A1 were in much better condition than the control mice and, except for two deaths, the animals appeared healthy until plus 48 hours. These results suggest that the antibody blocked the invasion of the blood stream by the bacteria and that once the protective antibody was exhausted, the mice rapidly died.

TABLE 8

The Effect of an Anti-LPS Antibody on Survival of Mice After Inoculation of a Burn Wound With *Pseudomonas aeruginosa* PA220.

| Monoclonal Antibody[a] | Immunization Time | % Mortality | Mean Time to Death (hr) |
|---|---|---|---|
| A2C6[b] | −24 h | 72.2 (13/18) | 44.6 ± 10.4[c] |
| 8A1[d] | −24 h | 75.0 (6/8) | 60.0 ± 13 |
| 8A1 | −24 h & +20 h[e] | 75.0 (6/8) | 76.6 ± 30.5[f] |

[a]Antibodies passively transferred intravenously at 0.4 ml per mouse.
[b]Anti-HBsAg monoclonal IgG1 at 4.0 mg/ml used as negative control.
[c]Standard Error of the Mean.
[d]Anti-LPS monoclonal IgG1 at 10.0 mg/ml
[e]At +20 h, 0.2 ml 8A1 given intravenously.
[f]Two mice died before 48 hours and the other 4 mice which eventually died appeared healthy at 48 hours.

Endotoxin Model

Lipopolysaccharides (LPS) are the endotoxins of gram-negative bacteria and play an important role in the pathogenicity of gram-negative infections. The biological activities of LPS are expressed in the lipid A component. For this reason an endotoxin shock model was used to check the efficacy of the anti-LPS monoclonals to neutralize the toxic effects of lipid A and Re LPS in vivo. Because mice are relatively resistant to the lethal effects of endotoxin, a galactosamine-induced sensitization procedure previously developed by Galanos et al., (1979) *Proc. Natl. Acad. Sci. U.S.A.* 75, 5939–5934 was used. This model allows the use of large overdoses of endotoxin.

Figure 5:
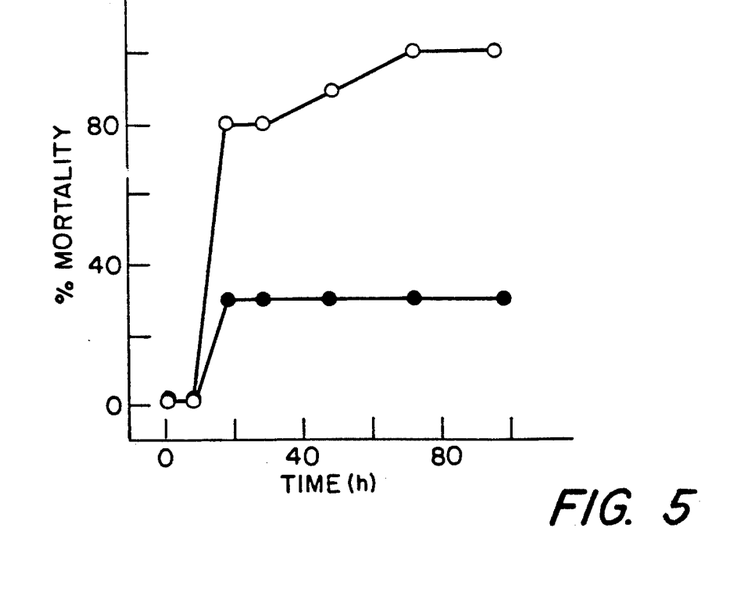
FIG. 5 shows in vivo neutralization of the lethal toxic effects of free lipid A by a mixture of 8A1 and 5E4 murine monoclonal anti-LPS antibodies.

In the first experiment a group of 10 CD-1 female mice (Charles River Breeding Laboratory, Kingston, N.Y.) received 10 mg of an equimolar mixture of monoclonals 8A1 and 5E4 via an intraperitoneal inoculation 40 hours before and again at 16 hours before challenge. Immediately before challenge, 12 ug of free lipid A, 15 mg galactosamine and 3 mg total of the 8A1 and 5E4 antibodies were mixed and administered via the tail vein. A group of control mice were treated identically except that PBS was substituted for the antibody mixture. Previous experiments had shown the 12.0 ug lipid A—15.0 mg galactosamine mixture to be approximately the minimum 100% lethal dose. The results shown in FIG. 5 clearly show the antibody mixture was able to partially neutralize the in vivo effects of lipid A.

Figure 6:
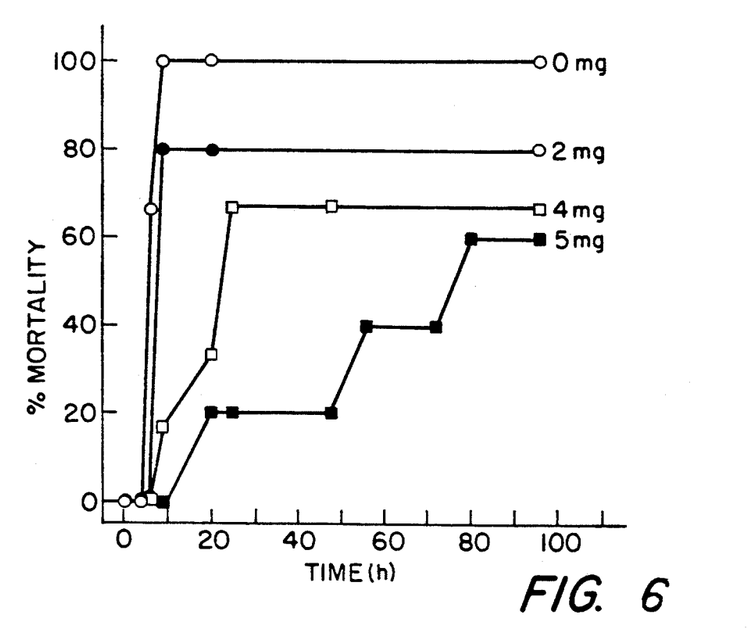
FIG. 6 shows the in vivo neutralization of the lethal toxic effects of S. minn. Re LPS by a mixture of the 8A1 and 4A10 murine monoclonal anti-LPS antibodies.

In a second experiment several doses of an equimolar mixture of two monoclonal antibodies, 4A10 and 8A1 were passively transferred into groups of 5-6 mice at 16 hours before endotoxin injection. In this case, 0.1 ug Re LPS and 15 mg galactosamine were used as the challenge agent. No antibody was premixed with the endotoxin in this mixture. This amount of Re LPS was found to be at least 100 $LD_{100}$ in dose experiments. As seen in FIG. 6, the antibody mixture clearly imparted significant protection to the mice from the lethal effects of the endotoxin in a dose dependent manner. A point not immediately apparent in FIG. 6 is that 4 out of 6 control mice were dead at 6 hours post challenge, yet no mouse receiving any dose of antibody had died by this time. It is apparent that the higher the antibody dose, fewer mice die and they die more slowly.

These experiments clearly demonstrate that the anti-LPS monoclonal antibodies can compete favorably with receptors in vivo for endotoxin.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A human monoclonal antibody which binds to a determinant found in the endotoxin core of gram-negative bacteria wherein said endotoxin core consists essentially of the lipid A and core oligosaccharide regions, and not the O-side chain region of bacterial lipopolysaccharide, and which is cross-reactive with endotoxin from different genera of gram-negative bacteria.

2. A hybridoma-produced monoclonal antibody which binds to a determinant in the endotoxin core of gram-negative bacteria wherein said endotoxin core consists essentially of the lipid A and core oligosaccharide regions, and not the O-side chain region of bacterial lipopolysaccharide, and which antibody is cross-reactive with endotoxin from different genera of gram-negative bacteria, said monoclonal antibody being produced by a human-human hybridoma.

3. A hybridoma-produced monoclonal antibody which binds to a determinant in the endotoxin core of gram-negative bacteria wherein said endotoxin core consists essentially of the lipid A and core oligosaccharide regions, and not the O-side chain region of bacterial lipopolysaccharide, and which antibody is cross-reactive with endotoxin from different genera of gram-negative bacteria, said monoclonal antibody being produced by a human-nonhuman hybridoma.

* * * * *